US008818494B2

(12) United States Patent
Zhang (10) Patent No.: US 8,818,494 B2
(45) Date of Patent: Aug. 26, 2014

(54) SYSTEM FOR VENTRICULAR FUNCTION ABNORMALITY DETECTION AND CHARACTERIZATION

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 413 days.

(21) Appl. No.: 13/184,662

(22) Filed: Jul. 18, 2011

(65) Prior Publication Data

US 2012/0136264 A1     May 31, 2012

Related U.S. Application Data

(60) Provisional application No. 61/417,497, filed on Nov. 29, 2010.

(51) Int. Cl.
*A61B 5/0402*     (2006.01)
*A61B 5/0452*     (2006.01)
*A61B 5/00*     (2006.01)
*A61B 5/04*     (2006.01)

(52) U.S. Cl.
CPC ............. *A61B 5/7257* (2013.01); *A61B 5/0452* (2013.01); *A61B 5/0402* (2013.01); *A61B 5/04014* (2013.01); *A61B 5/7203* (2013.01)
USPC .......................................... 600/509; 600/515

(58) Field of Classification Search
CPC ............... A61B 5/0452; A61B 5/0472; A61B 2018/0898
USPC ................................................ 600/509, 515
See application file for complete search history.

(56) References Cited

U.S. PATENT DOCUMENTS

| 4,681,117 A | 7/1987 | Broadman |
| 4,798,211 A | 1/1989 | Goor et al. |
| 4,924,875 A | 5/1990 | Chamoun |
| 4,930,075 A | 5/1990 | Kortas |
| 5,054,496 A | 10/1991 | Wen et al. |
| 5,159,932 A | 11/1992 | Zanetti et al. |
| 5,365,426 A | 11/1994 | Siegel et al. |
| 6,024,705 A | 2/2000 | Schlager et al. |

(Continued)

OTHER PUBLICATIONS

Stuart E. Sheifer, MD; Teri A. Manolio, MD, PhD; and Bernard J. Gersh, MB, ChB, DPhil, "Unrecognized Myocardial Infarction", Annals of Internal Medicine, Nov. 6, 2001, vol. 135 Issue 9, pp. 801-811.

(Continued)

*Primary Examiner* — Christopher D Koharski
*Assistant Examiner* — Natasha Patel
(74) *Attorney, Agent, or Firm* — Brennan K Bradley (57) ABSTRACT

A system for heart performance characterization and abnormality detection includes an interface for receiving signal data representing an electrical signal indicating electrical activity of a patient heart over multiple heart beat cycles. A filter extracts first signal component data in a first selected bandwidth and first heart cycle portion of the received signal data and second signal component data in a different second selected bandwidth and second heart cycle portion of the received signal data. A signal processor uses the received signal data in calculating a ratio of a first value derived from the first signal component data to a second value derived from the second signal component data. A patient monitor in response to the calculated ratio or value derived from the calculated ratio, generates an alert message associated with the threshold.

23 Claims, 10 Drawing Sheets

(56) References Cited

U.S. PATENT DOCUMENTS

| | | | |
|---|---|---|---|
| 6,112,116 | A | 8/2000 | Fischell et al. |
| 6,339,720 | B1 | 1/2002 | Anzellini et al. |
| 6,368,284 | B1 | 4/2002 | Bardy |
| 6,424,860 | B1 | 7/2002 | Karlsson et al. |
| 6,468,263 | B1 | 10/2002 | Fischell et al. |
| 6,501,983 | B1 | 12/2002 | Natarajan et al. |
| 6,882,883 | B2 | 4/2005 | Condie et al. |
| 7,072,708 | B1 | 7/2006 | Andresen et al. |
| 7,181,268 | B2 | 2/2007 | Sheldon et al. |
| 7,225,015 | B1 | 5/2007 | Min et al. |
| 7,231,244 | B2 | 6/2007 | Laitio et al. |
| 7,266,410 | B2 | 9/2007 | Chen |
| 7,277,745 | B2 | 10/2007 | Natarajan et al. |
| 7,299,087 | B2 | 11/2007 | Bardy et al. |
| 7,361,473 | B2 | 4/2008 | Valkirs et al. |
| 7,415,307 | B2 | 8/2008 | Sharma et al. |
| 7,542,794 | B1 | 6/2009 | Zhang et al. |
| 2007/0129639 | A1 | 6/2007 | Zhang et al. |
| 2009/0281441 | A1* | 11/2009 | Zhang et al. .......... 600/516 |

OTHER PUBLICATIONS

S Abboud, RJ Cohen, A Selwyn, P Ganz, D Sadeh and PL Friedman, "Detection of transient myocardial ischemia by computer analysis of standard and signal-averaged high-frequency electrocardiograms in patients undergoing percutaneous transluminal coronary angioplasty", Circulation, vol. 76, 585-596.

Hamilton, Patrick S.; Tompkins, Willis J., "Quantitative Investigation of QRS Detection Rules Using the MIT/BIH Arrhythmia Database", IEEE Transactions on Biomedical Engineering, Issue Date: Dec. 1986, vol. BME-33 Issue:12, pp. 1157-1165.

Huiskamp, G.; van Oosterom, A., "The depolarization sequence of the human heart surface computed from measured body surface potentials", IEEE Transactions on Biomedical Engineering, vol. 35, Issue: 12, Publication Year: 1988, pp. 1047-1058.

Greensite, F.; Huiskamp, G., "An improved method for estimating epicardial potentials from the body surface", IEEE Transactions on Biomedical Engineering, vol. 45, Issue: 1, Publication Year: 1998, pp. 98-104.

Huiskamp, G., "Simulation of depolarization in a membrane-equations-based model of the anisotropic ventricle", IEEE Transactions on Biomedical Engineering, vol. 45, Issue: 7, Publication Year: 1998, pp. 847-855.

Laguna, P.; Thakor, N.V.; Caminal, P.; Jane, R., "Low-pass differentiators for biological signals with known spectra: application to ECG signal processing", IEEE Transactions on Biomedical Engineering, vol. 37, Issue: 4, Publication Year: 1990, pp. 420-425.

Olivier Meste, Nerve Rix, Nitish, Thakor, "Ventricular late potentials characterization in time-frequency domain by means of a wavelet transform", IEEE transactions on Biomedical engineering, vol. 41, No. 7, Jul. 1994, p. 625-634.

Vidosav Stojanovć1, Siniša Minić, "Finite Impulse Response Digital Filters with Integer Multipliers" Serbian Journal of Electrical Engineering, vol. 1, No. 1, Nov. 2003, p. 131-141.

Gramatikov B; Brinker J; Yi-chun S; Thakor N V, "Wavelet analysis and time-frequency distributions of the body surface ECG before and after angioplasty", Computer methods and programs in biomedicine 2000; vol. 62(2), p. 87-98.

R. Warlar and C. Eswaran, "Integer coefficient bandpass filter for the simultaneous removal of baseline wander, 50 and 100 Hz interference from the ECG", Medical and Biological Engineering and Computing vol. 29, No. 3, p. 333-336.

* cited by examiner

| Signal names | | Signal function and definition |
|---|---|---|
| Ventricular depolarization signals and activities (mainly QRX complex portion in the heart beat) | $VD_1$ | 1- 20 Hz ventricular depolarization which is define as low frequency depolarization component signal |
| | $VD_2$ | 20-40 Hz ventricular depolarization which is define as mid-1 frequency depolarization component signal |
| | $VD_3$ | 40-80 Hz ventricular depolarization which is define as mid-2 frequency depolarization component signal |
| | $VD_4$ | 80-120 Hz ventricular depolarization which is define as high-1 frequency depolarization component signal |
| | $VD_5$ | 120-200 Hz ventricular depolarization which is define as high-2 frequency depolarization component signal |
| Ventricular Repolarization signals and activities (mainly T wave portion in the heart beat) | $VR_1$ | 1-10 Hz ventricular repolarization which is defined as low frequency repolarization component signal |
| | $VR_2$ | 10-20 Hz ventricular repolarization which is defined as middle frequency repolarization component signal |
| | $VR_3$ | 20-40 Hz ventricular repolarization which is defined as high frequency repolarization component signal |

| Ratio names | Definition and calculation |
|---|---|
| Depolarization to Depolarization ratios | The ratio compares two depolarization sub-component signals, for example between $VD_2$ and $VD_1$.<br><br>Energy ratio: $\mu_{VD_1-VD_2} = \dfrac{E(VD_1)}{E(VD_2)}$<br><br>Energy fraction ratio: $\mu_{VD_1\_fraction} = \dfrac{E(VD_1)}{E(QRS+T)}$<br><br>Entropy ratio: $\mu_{entropy\_VD_1\_VD_2} = \dfrac{Entropy(VD_1)}{Entropy(VD_2)}$<br><br>Entropy fraction ratio: $\mu_{entropy\_VD_1\_fraction} = \dfrac{Entropy(VD_1)}{Entropy(QRS+T)}$<br><br>This ratio may comprise two components assocated with ventricular depolarization: $VD_j$ and $VD_i$<br>The component signals may be a combination of several ventricular depolarization sub-bandwidth components, $VD_N$, $VD_N = \sum_{i \in N} VD_i$ |
| Repolarization to Repolarization ratios | The ratio compares two repolarization sub-component signals, for example $VR_2$ and $VR_1$.<br><br>Energy ratio: $\mu_{VR_1-VR_2} = \dfrac{E(VR_1)}{E(VR_2)}$<br><br>Energy fraction ratio: $\mu_{VR_1\_fraction} = \dfrac{E(VR_1)}{E(QRS+T)}$<br><br>Entropy ratio: $\mu_{entropy\_VR_1\_VR_2} = \dfrac{Entropy(VR_1)}{Entropy(VR_2)}$<br><br>Entropy fraction ratio: $\mu_{entropy\_VR_1\_fraction} = \dfrac{Entropy(VR_1)}{Entropy(QRS+T)}$<br><br>The ratio also comprises two components assocated with ventricular repolarization: $VR_j$ and $VR_i$<br>The component signals may comprise a combination of several ventricular repolarization sub-bandwidth components, $VR_M$, $VR_M = \sum_{i \in M} VR_i$ |

Figure 7

| Ratio names | Definition and calculation | |
|---|---|---|
| Depolarization to Repolarization ratios (bi-lateral ratio) | The ratio compares two sub-component signals (one is a depolarization sub-bandwidth component signal and one is a repolarization sub-bandwidth component signal), for example $VD_1$ and $VR_1$.<br><br>Energy ratio: $\mu_{VD_1-VR_1} = \dfrac{E(VD_1)}{E(VR_1)}$<br><br>Entropy ratio: $\mu_{entropy\_VD_1\_VR_1} = \dfrac{Entropy(VD_1)}{Entropy(VR_1)}$<br><br>The ratio may also comprise two components associated with ventricular depolarization and repolarization: $VD_j$ and $VR_i$<br><br>The component signals may be a combination of multiple ventricular depolarization and repolarization sub bandwidth components, $VD_N$ and $VR_M$ | 703 |
| Multi-component ratios | The ratio compares Multi sub-component signals (some are depolarization sub-bandwidth component signals and some are repolarization sub-bandwidth component signals), for example between N depolarization component signals $VD_N$ and M repolarization component signals $VR_M$.<br><br>Energy ratio: $\mu_{VD_N-VR_M} = \dfrac{E(VD_N)}{E(VR_M)}$<br><br>Entropy ratio: $\mu_{entropy\_VD_N\_VR_M} = \dfrac{Entropy(VD_N)}{Entropy(VR_M)}$ | 705 |

SYSTEM FOR VENTRICULAR FUNCTION ABNORMALITY DETECTION AND CHARACTERIZATION

This is a non-provisional application of provisional application Ser. No. 61/417,497 filed Nov. 29, 2010, by H. Zhang.

FIELD OF THE INVENTION

This invention concerns a system for heart performance characterization and abnormality detection based on characteristics of signal components in different selected bandwidths and different heart cycle portions of a received signal representing heart electrical activity of a patient.

BACKGROUND OF THE INVENTION

Ventricular arrhythmia detection is necessary for the management of cardiac disorders and irregularities, which may be caused by a lack of blood, oxygen, in the heart tissue and cells. Usually analysis of non-invasive surface ECG signal and invasive intra-cardiac electrograms based on waveform morphology and time domain parameters is used for ventricular abnormality detection and characterization, such as by analyzing QRS complex and T wave changes. Early arrhythmia recognition and characterization, such as of ventricular tachycardia and myocardial ischemia (MI), is desirable for rhythm management of cardiac disorders and irregularities before a rhythm progresses to a life-threatening arrhythmia, such as infarction and fibrillation. Known waveform morphology and time domain parameter analysis of depolarization and repolarization processes, such as of a P wave, QRS complex, ST segment, T wave, is used for cardiac arrhythmia monitoring and identification, e.g. of atrial fibrillation (AF), myocardial ischemia and ventricular tachycardia/fibrillation (VT/VF). Typically a 12-lead electrocardiogram (ECG) and multi-channel intra-cardiac electrogram (ICEG from invasive cardiac catheters) are used for evaluation of a cardiac rhythm and events.

Known clinical systems (such as for ST segment analysis and P wave morphology detection), which perform waveform and time domain parameter analyses, are sometimes inaccurate and time-consuming. These Known electrophysiological signal (including ECG, ICEG signal) processing systems also require extensive clinical knowledge and experience. Inaccurate and subjective evaluation and diagnosis may delay cardiac rhythm management. Further, known systems usually focus on time (amplitude, latency) or frequency (power, spectrum) domain changes and analysis, which may not efficiently and accurately capture and characterize small signal changes in a portion of a cardiac signal. Consequently, known systems may have a high failure rate of arrhythmia diagnosis and increased false alarm generation. Known methods for ventricular arrhythmia diagnosis typically focus on events and involve qualitative detection and are prone to generate false alarms due to single parameter analysis, such as analysis of a magnitude of ST segment exceeding a 0.1 mV threshold. A system according to invention principles addresses these deficiencies and related problems.

SUMMARY OF THE INVENTION

A system analyzes cardiac electrophysiological signals (including surface ECG signals and internal cardiac electrograms, ICEG signals) based on ventricular component signal characteristics of different bandwidths of a heart electrical activity over a cardiac cycle. A system for heart performance characterization and abnormality detection includes an interface for receiving signal data representing an electrical signal indicating electrical activity of a patient heart over multiple heart beat cycles. A filter extracts first signal component data in a first selected bandwidth and first heart cycle portion of the received signal data and second signal component data in a different second selected bandwidth and second heart cycle portion of the received signal data. A signal processor uses the received signal data in calculating a ratio of a first value derived from the first signal component data to a second value derived from the second signal component data. A comparator compares the calculated ratio or value derived from the calculated ratio with a threshold value to provide a comparison indicator. A patient monitor in response to the comparison indicator indicating a calculated signal characteristic value exceeds the threshold value, generates an alert message associated with the threshold.

DETAILED DESCRIPTION OF THE INVENTION

A system analyzes cardiac electrophysiological signals (including surface ECG signals and internal cardiac electrograms, ICEG signals) based on ventricular component signal ratios of different bandwidth (sub-bandwidth) within a cardiac cycle. The system performs a sub-bandwidth signal measurement and ratio calculation including of 1) Sub-bandwidth component signal energy ratio; 2) Sub-bandwidth component signal entropy ratio; 3) combined Sub-bandwidth component ratio index and overall signal ratio. The calculated parameters are used in the real time monitoring and analysis and may be used in implantable devices and for evaluation of effects of drug delivery. The system is usable for detection of different ventricular arrhythmias, such as myocardial infarction and ventricular tachycardia and fibrillations.

The principal manifestations of coronary artery disease (CAD) are coronary artherosclerosis (hardening of the coronary arteries) or stenosis (narrowing of the arteries), both of which ultimately force a reduction in the coronary circulation (such as myocardial ischernia, or infarction, in the ventricle). During ischemia and infarction, various portions of heart muscle receive less oxygen which can ultimately lead to irreversible scarring and necrosis of the muscle tissue (myocardial infarction), reducing the efficiency with which the heart can pump blood to the rest of the body and possibly leading to fatal cardiac arrhythmias, such as tachycardia or fibrillation.

A Ventricle comprises a chamber of the heart which controls the blood flow and oxygen distribution to a region of the whole heart and the whole body. The cells of a ventricle respond by altering tissue action potentials. The changes in these individual cells manifest in local electrograms during depolarization and repolarization, reducing signal energy (hyperkalemia or anoxia) or creating multi-phasic waveforms (decoupling) or waveform morphologies. These abnormal behaviors in relatively small regions of the heart, lumped together with the rest of the heart, cause notches and slurs of small amplitude superimposed on largely normal electrograms including both surface ECG signals and intra-cardiac electrograms. Small ventricle arrhythmias may cause severe heart function/activity pathologies and even death. Ventricular activity and signal monitoring may facilitate earlier, more accurate and reliable detection, characterization and treatment of ventricular arrhythmias.

The system associates different bandwidths of a heart electrical activity signal with different electrophysiological characteristics of cardiac function, such as fast to slow wave activity in a ventricle. The system decomposes a patient cardiac electrophysiological signal into sub-signal components of different frequency bandwidth where the bandwidths are selected in response to data indicating a clinical application and a procedure being performed. Sub-bandwidth component ratios are calculated to identify sub-signal changes due to ventricular pathologies, by comparing sub-component signal entropy and energy. The calculated signal ratios are used to detect cardiac arrhythmia (mainly myocardial ischemia and infarction) analysis.

Figure 1:
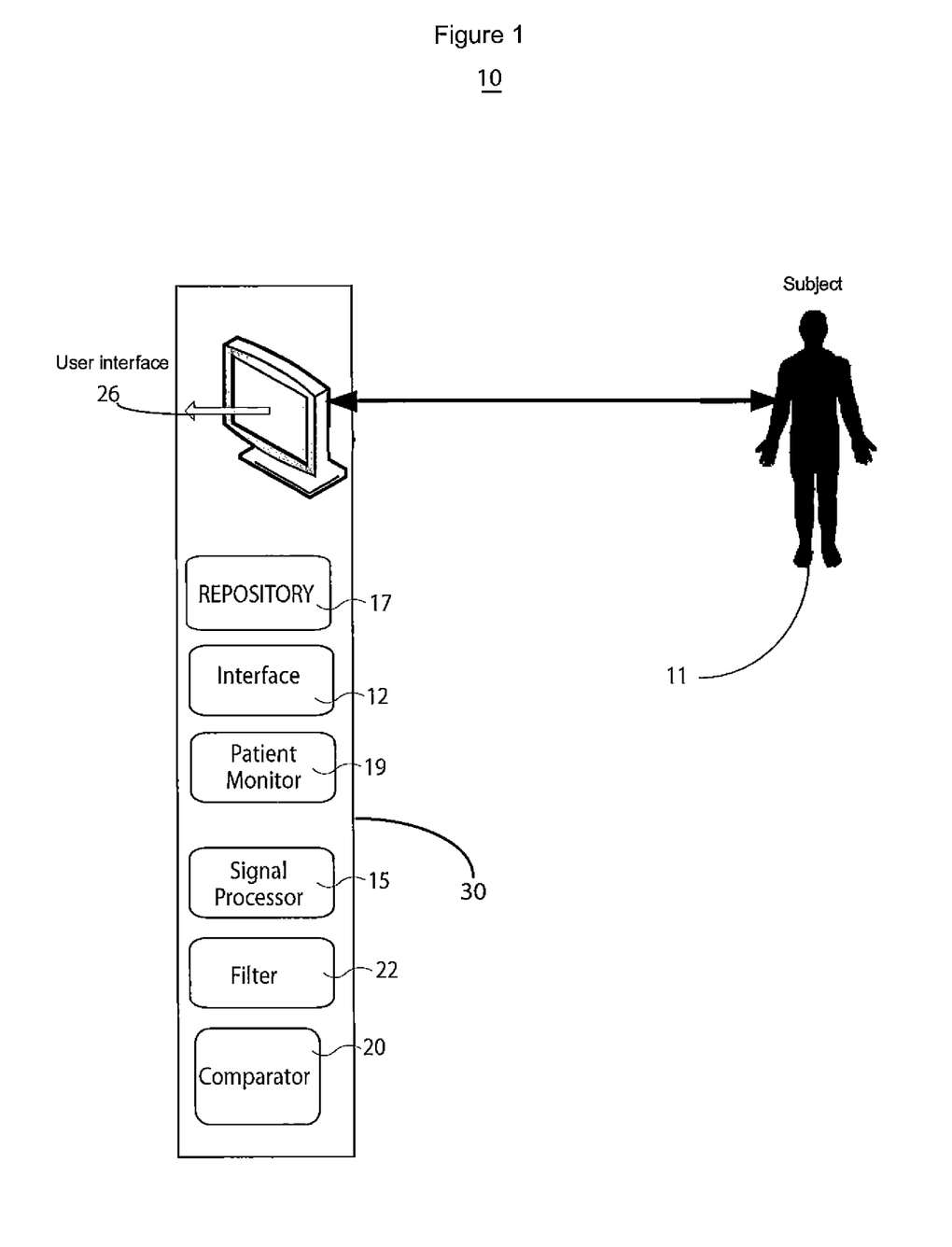
FIG. 1 shows a system for heart performance characterization and abnormality detection, according to invention principles.

FIG. 1 shows system 10 for heart performance characterization and abnormality detection. System 10 comprises at least one computer system, workstation, server or other processing device 30 including interface 12, repository 17, filter 22, patient monitor 19, signal processor 15, comparator 20 and a user interface 26. Interface 12 receives signal data representing an electrical signal indicating electrical activity of a patient heart over multiple heart beat cycles. Filter 22 extracts first signal component data in a first selected bandwidth and first heart cycle portion of the received signal data and second signal component data in a different second selected bandwidth and second heart cycle portion of the received signal data. Signal processor 15 uses the received signal data in calculating a ratio of a first value derived from the first signal component data to a second value derived from the second signal component data. Comparator 20 compares the calculated ratio or value derived from the calculated ratio with a threshold value to provide a comparison indicator. Patient monitor 19, in response to the comparison indicator indicating a calculated signal characteristic value exceeds the threshold value, generates an alert message associated with the threshold.

A heart beat cycle involves electrophysiological signals associated with different chambers, atrial and ventricular, such as P wave, Q wave, R wave, S wave, T wave and U wave signal segments. Different portions of the cardiac signal represent activities of different portions of the heart and tissue, e.g., a P wave for atrium, QRS for depolarization of a ventricle and T wave for repolarization of a ventricle. Signals from different portions of the heart lie in different bandwidths (in the frequency domain). For example, a T wave (ventricular repolarization) occupies a low frequency band: 5-20 Hz and a QRS complex wave (ventricular depolarization) occupies a relatively high frequency band: 25-100 Hz.

Figure 2:
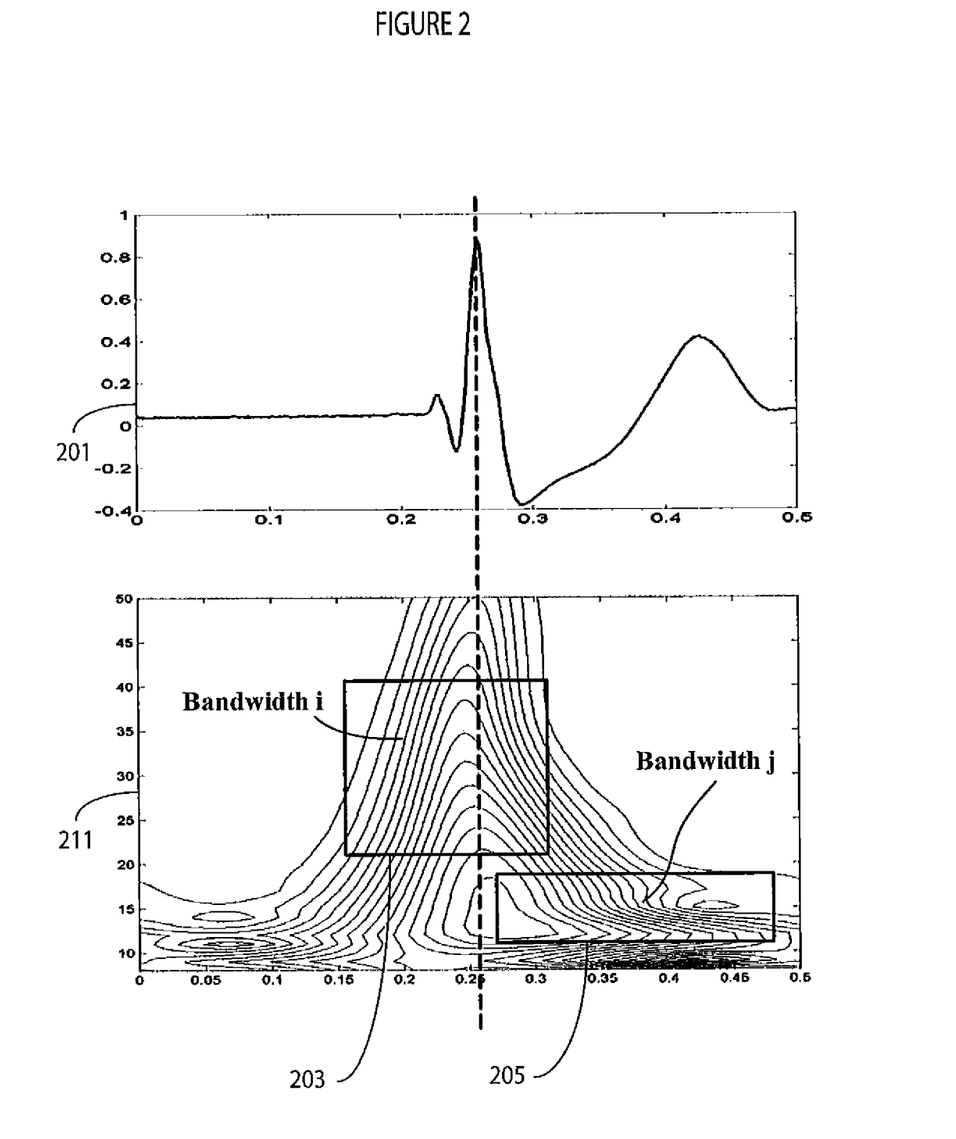
FIG. 2 shows cardiac signal time and corresponding frequency domain signal distribution and bandwidth selection, according to invention principles.

FIG. 2 shows a single heart cycle cardiac signal time domain waveform 201 and corresponding frequency domain distribution 211 and bandwidth selection. The QRS complex signals may have a peak value up to 200 Hz. The system uses multiple heart beat signals for averaging to improve signal to noise ratio (e.g., using an averaging and shifting window of 5 to 15 heart beats of a signal, for example, depending on a determined noise level of an electrophysiological signal). In addition, sub-component signals are determined based on time, for example, ventricular depolarization 203 (Bandwidth i) or repolarization signals 205 (Bandwidth j). In the time domain, a QRS wave and T wave are shown. In the frequency domain a first signal component comprising a QRS wave associated with ventricular depolarization has a first selected bandwidth 203. A second signal component comprising a T wave associated with ventricular repolarization has a second selected bandwidth 205. In a clinical application, system 10 (FIG. 1) uses multiple component analysis to track and characterize ventricular signal changes and arrhythmias. In order to improve sensitivity and stability of ventricular detection and evaluation, heart signals (ventricular signals and electrophysiological signals) are divided into multi-component sub-signals based on both time domain function and frequency ROI areas.

Figure 3:
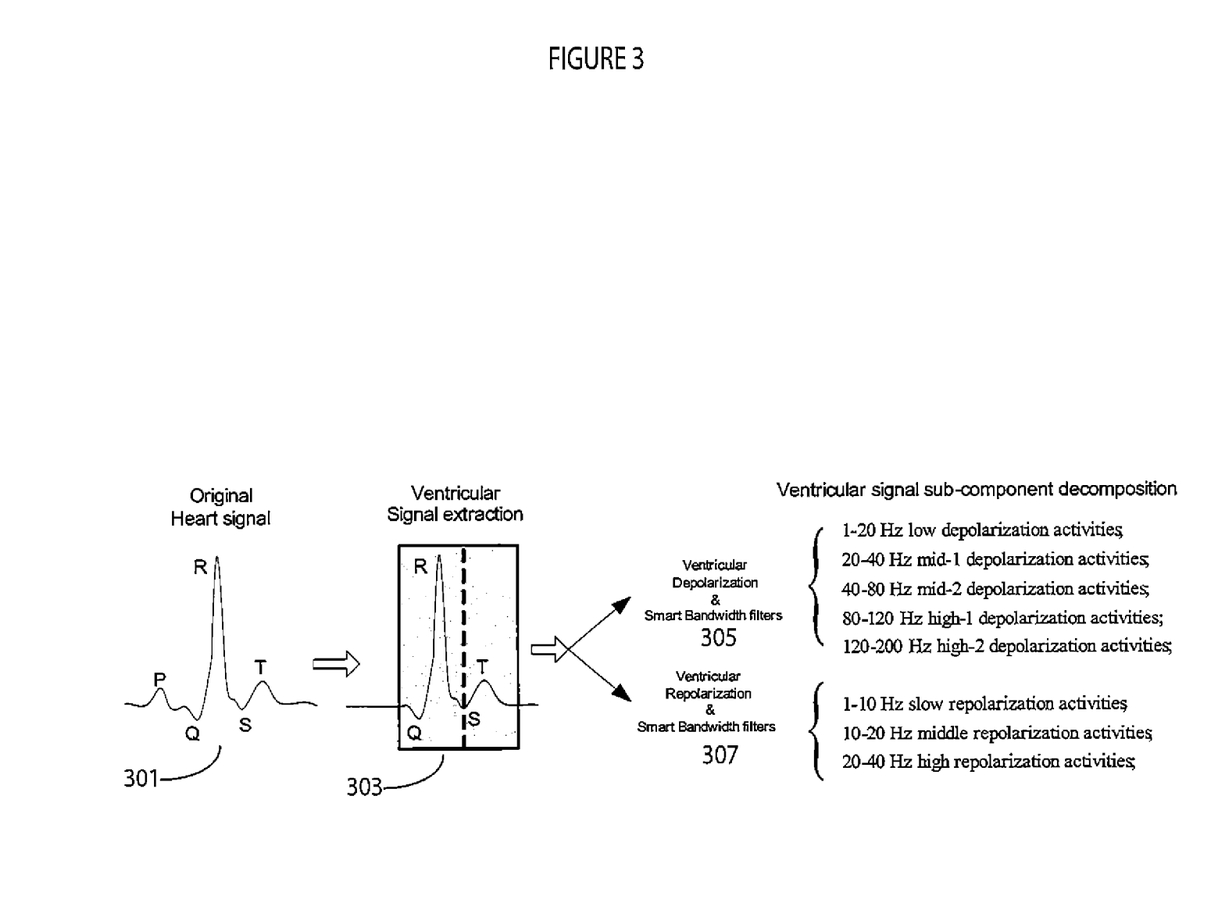
FIG. 3 shows signal component extraction and separation for ventricular electrophysiological signal analysis, according to invention principles.

FIG. 3 shows signal component extraction and separation for ventricular electrophysiological signal analysis. Signal extraction unit 303 (e.g. within signal filter 22 FIG. 1) extracts sub-component signals associated with ventricular activities from heart activity signal 301 using different filters, such as band-pass filters and low and high pass filters. Unit 303 uses integer coefficients or quantitized coefficient filters to reduce calculation complexity and time. Unit 303 performs ventricular signal extraction (from the beginning of a Q wave to the end of a T wave including extracting components associated with both ventricular depolarization and repolarization activities. Unit 303 uses a smart bandwidth filter configured for extracting a QRS portion and to separate a ventricular depolarization signal into sub-signal components. Unit 303 uses a smart bandwidth filter configured for extracting a T wave (including an ST segment) and to separate a ventricular repolarization signal into sub-signal components. Unit 303 further uses bandwidth filters for deriving different sub-signal components for further diagnosis and calculation. Unit 303 extracts repolarization component signals 307 (from S wave to the end of T wave) comprising bandwidths including 1-10 Hz slow repolarization activities, 10-20 Hz middle repolarization activities and 20-40 Hz high repolarization activities.

Figure 4:
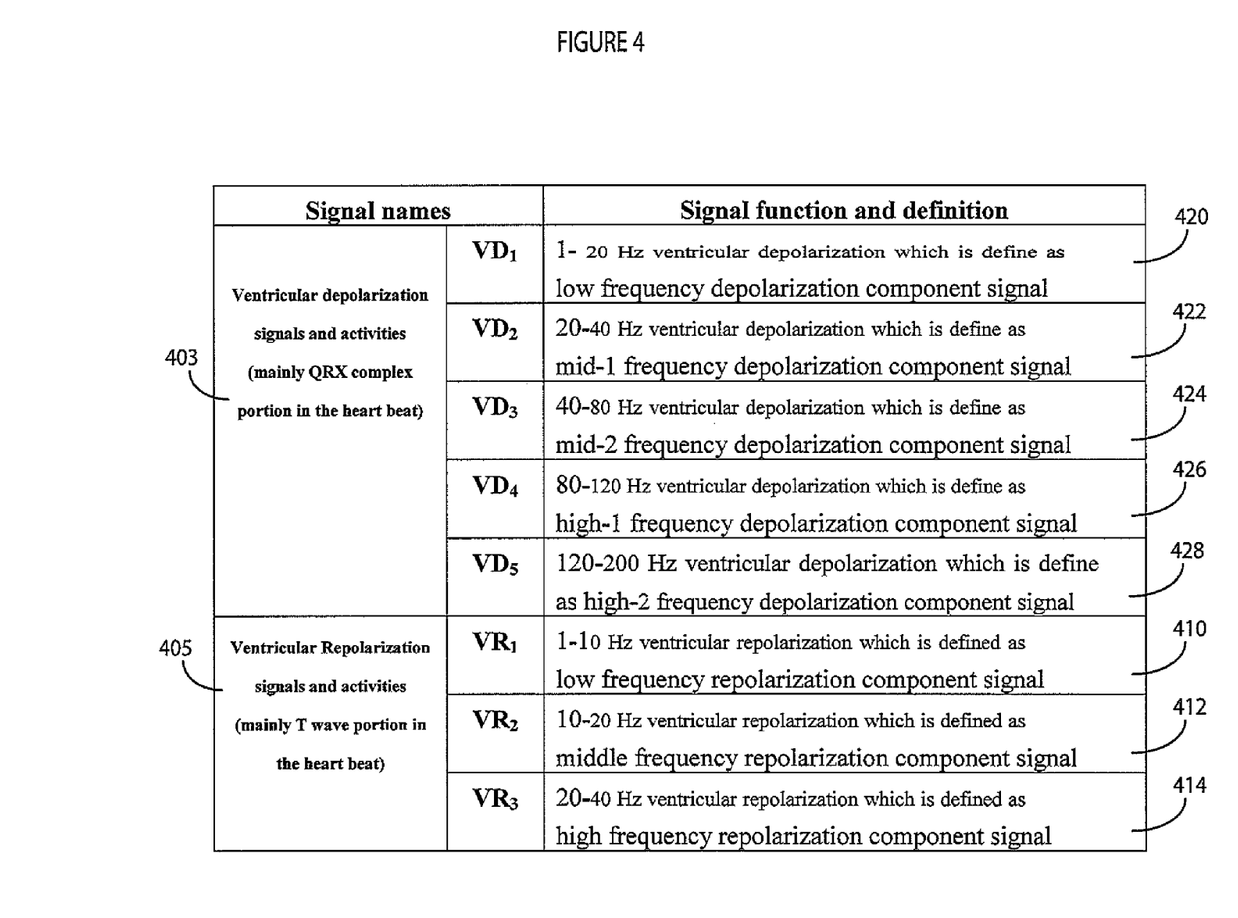
FIG. 4 comprises a table showing identified signal component bandwidths and associated ventricular functions and activities, according to invention principles.

Unit 303 extracts depolarization component signals 305 (from Q wave to S wave) comprising bandwidths including 1-20 Hz low depolarization activities, 20-40 Hz mid-1 depolarization activities, 40-80 Hz mid-2 depolarization activities, 80-120 Hz high-1 depolarization activities and 120-200 Hz high-2 depolarization activities. Unit 303 filters out a 0-1 Hz sub-component signal associated with respiration signals and other patient biological noise. FIG. 4 comprises a table showing identified depolarization signal component 403 bandwidths VD1, VD2, VD3, VD4 and VD5 (420, 422, 424, 426 and 428). The table also shows identified repolarization signal component 405 bandwidths VR1, VR2 and VR3 (410, 412 and 414). Individual sub-component signals in the table may be used for diagnosis and characterization of different arrhythmias, for example $VD_2$ and $VR_2$ are usually utilized for myocardial ischemia and infarction analysis and evaluation. In a different clinical application, a different definition of sub-bandwidth signal components is used including, for example, $VD_{11}$ comprising a 15-25 Hz bandwidth and $VR_{21}$ comprising a 20-30 Hz bandwidth. Different bandwidth component signals reflect different activities. Electrophysiological signals of a ventricle are used to detect early abnormality in ventricular function, for example. The different bandwidth component separation, extraction, combination and definition is adaptively, automatically performed in response to user input or system command.

Figure 5:
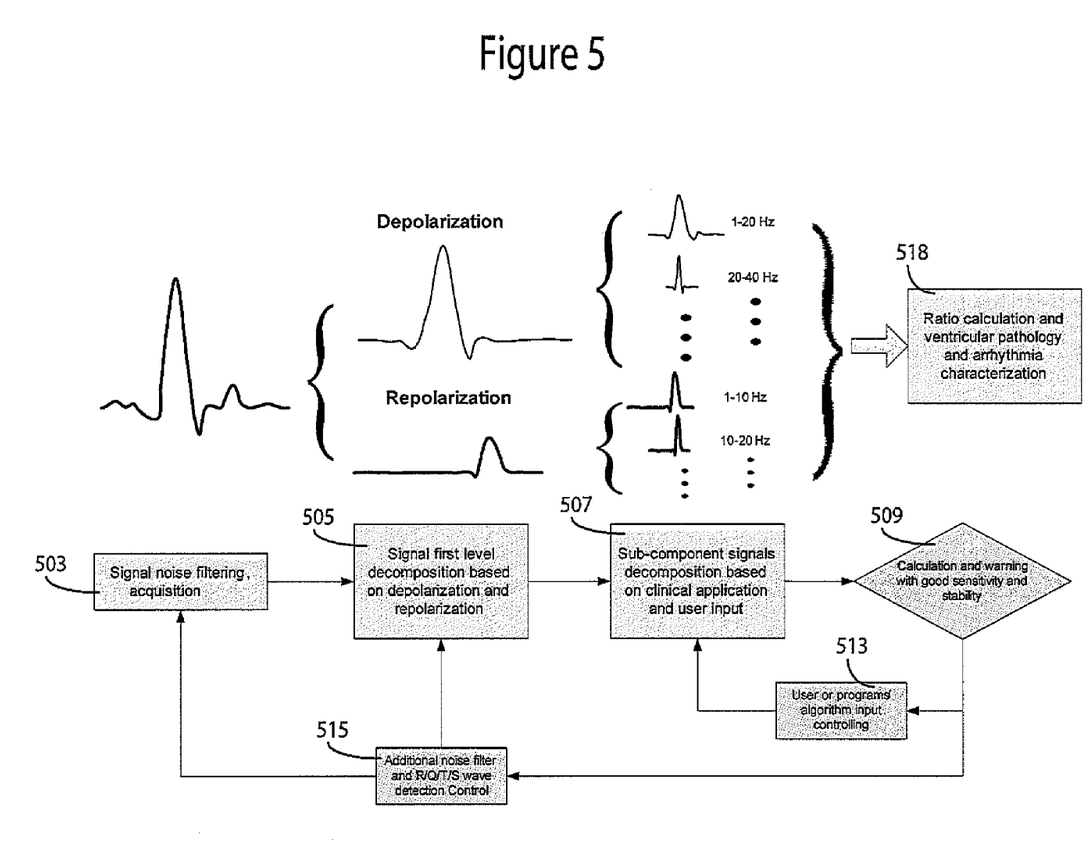
FIG. 5 shows a system for signal component decomposition and analysis, according to invention principles.

FIG. 5 shows a system for signal component decomposition, analysis and associated calculations for ventricular arrhythmia detection and analysis. Unit 503 acquires and filters a heart activity signal using high, low and band pass filters and choke filters to cancel common mode noise. Unit 505 performs first level cardiac signal decomposition of the filtered signal for ventricular depolarization and repolarization and performs RR, Q, S, T wave detection. Unit 507 performs second level sub-component signal decomposition in response to user input or system command and determines frequency components of a ROI for further component ratio analysis. Unit 518 performs ratio calculation and ventricular arrhythmia diagnosis and characterization to detect an ischemia event in left ventricular tissue, for example. Unit 509 generates an alert message in response to detection of a medical condition associated with a calculated parameter and unit 513 adjusts calculation characteristics and repeats calculation and detection of units 507 and 509. Unit 515 adaptively adjusts filter and wave detection and decomposition characteristics in response noise detection and quantification. The system uses different types of calculation to track small changes in ventricular activities.

Figure 6:
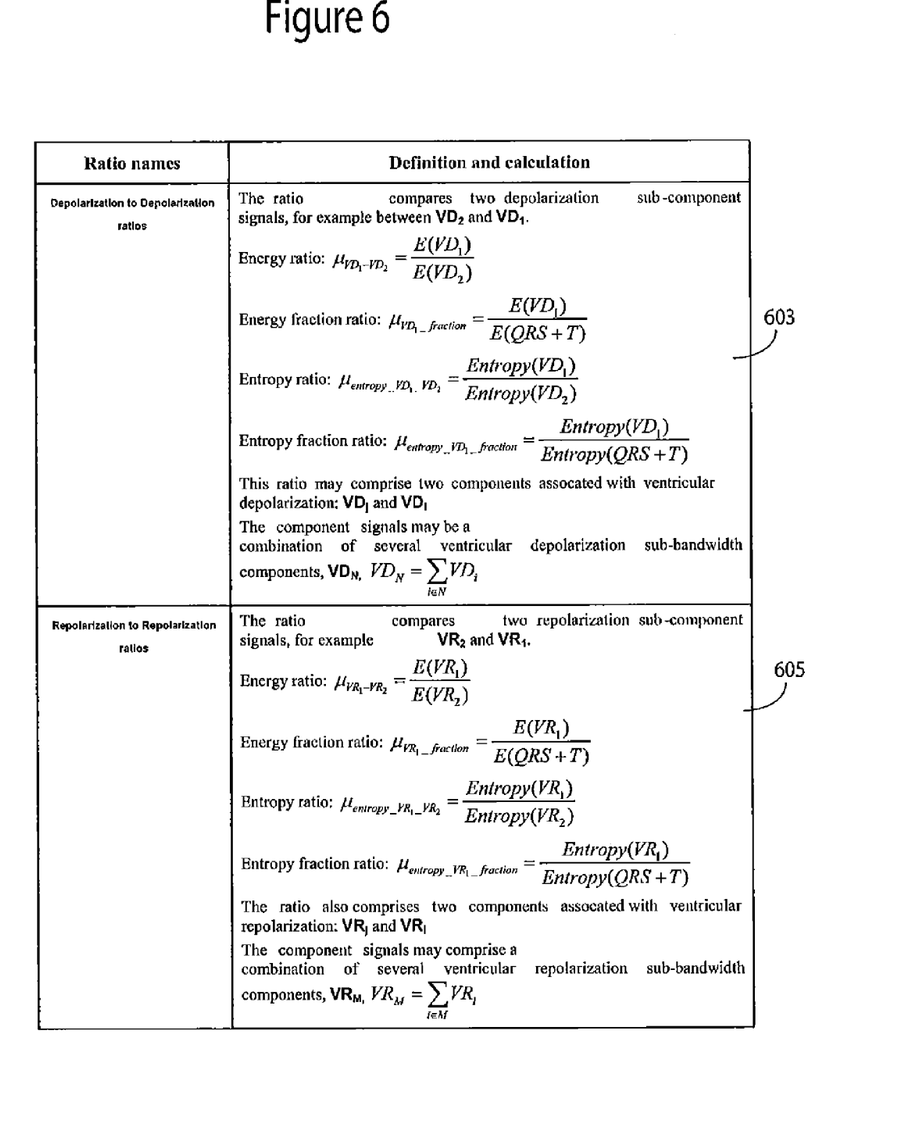
FIGS. 6 and 7 comprise a table showing parameters and ratios calculated by a system for heart performance characterization, according to invention principles.
Figure 7:
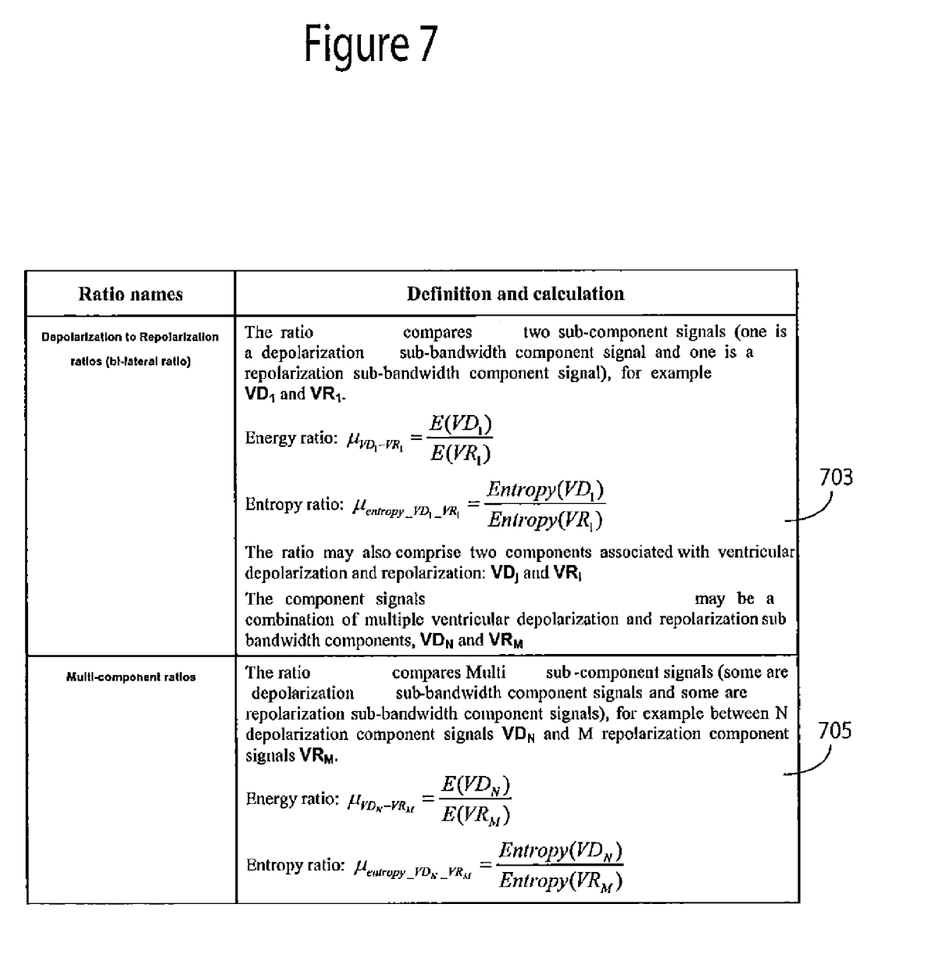

FIGS. 6 and 7 comprise a table showing parameters and ratios calculated by a system for heart performance characterization. Table area 603 shows depolarization to depolarization ratios and Table area 605 shows repolarization to repolarization ratios. Table area 703 shows depolarization to repolarization ratios and Table area 705 shows multiple component ratios.

Energy of a component signal or signals is:

$$\text{Energy: } E(\text{sub\_bandwidth\_component\_signal}) = \sum_{i \in \text{signal\_Q}} |V_Q(i)|^2$$

Where a sub_bandwidth_signal is one signal or a combination of ventricular depolarization or repolarization component signals; $V_Q(i)$ is a discrete digitized value set of ventricular sub-component signal Q (either depolarization or repolarization). The energy is determined based on time domain magnitude $V_Q(i)$ and in other embodiments the system uses other types of energy calculations, such as spectrum, frequency magnitude and frequency peak value (dominant frequency). There are different kinds of entropy that may be used n the table of FIGS. 6 and 7 including Shannon entropy used for a component signal or signals as:

$$\text{entropy}(\text{sub\_bandwidth\_signal}) = -\sum_{\substack{i=1 \\ x \in \text{sub\_bandwidth\_component}}}^{z} p(x_i) \log(p(x_i))$$

where a sub_bandwidth_signal is a signal or combination of ventricular depolarization or repolarization component signals; $x_i$ is discrete digital data within the sub_bandwidth_signal; $p(x_i)$ is the probability of the $x_i$ with in the sub_bandwidth_signal; Z is the total number of the digital data set of the sub_bandwidth_signal.

The system calculates multiple ratios and an overall signal ratio is computed based on multiple sub-bandwidth component signal ratios:

$$\text{ventricular signal ratio index: } \Re_{Ventricle} = \sum_{i \in \text{ratio\_combination}} \gamma_i(t) \mu_i$$

where, i is a number of a calculated ratio and derived for calculation of a ventricular signal and function ratio index; $\mu_i$ is the ratio computed for a sub-bandwidth component of a ventricular depolarization and repolarization signal; $\gamma_i(t)$ is the weight for each ratio in the combination calculation and $\mu_i$ may be programmable and time varying and adaptively updated by the system or a user. $\Re_{Ventricle}$ index value is utilized for different kinds of ventricular arrhythmia detection, diagnosis and characterization, such as myocardial ischemia and infarction event detection and evaluation, e.g. ischemia event occurrence and ischemia event severity, and to predict a critical time of an infarction event and treatment (such as a medicine administration time). $\Re_{Ventricle}$ calculation is used for ventricle function monitoring and diagnosis, and for monitoring other cardiac functions (such as atrial function and waveforms) and for other patient signal analysis (such as of an SPO2 waveform, respiration signals, O2 and blood pressure signals).

In complex clinical cases, ventricular signal ratio $\Re_{Ventricle}$ provides a sensitive characterization and reduces false alarms, especially where cardiac signals may involve substantial noise, such as in an ICD patient application. The table of FIGS. 6 and 7 show different kinds of ratio calculations and ratio definitions used for different sub-component signals which are associated with ventricular depolarization and repolarization procedures. Ratio changes are used to achieve real time monitoring and diagnosis of a ventricular function and tissue health status. For example, energy ratio $$\mu_{VD_2 - VR_2} = \frac{E(VD_2)}{E(VR_2)}$$

is an energy ratio of second ventricular depolarization component signal (20-40 Hz mid-1 frequency component signal) and second ventricular repolarization component signal (10-20 Hz middle frequency component). The ratio is used for detection and diagnosis. In an example, two episodes of ventricular activities are compared comprising normal and early infarction episodes. During normal status, the energy ratio $\mu_{VD_2 - VR_2}$ is 25.5. During an early myocardial infraction (Left ventricle) the ratio $\mu_{VD_2 - VR_2}$ is 37.3. Energy ratio $\mu_{VD_2 - VR_2}$ shows 47% variation. Typically in clinical application, 10-20% is set as a warning threshold for ventricular arrhythmia and abnormality (different level thresholds may be used for triggering a warning and characterization of different ventricular arrhythmia severity). Hence a 47% (>20%) change of energy ratio $$\mu_{VD_2-VR_2} = \frac{E(VD_2)}{E(VR_2)}$$

indicates there may be a ventricular myocardial ischemia and infarction abnormality event.

In order to improve the sub-bandwidth component ratio based ventricular function diagnosis and evaluation, the system employs statistical evaluation methods to quantify and characterize signal changes for ventricular arrhythmia severity determination. Functions used for characterizing ventricular signal changes include derived parameter and ratio variation and variability calculations including, $$\text{Mean or averaging value (expectation); mean}(X) = \frac{1}{N} \sum_{i \in N} X(i);$$

$$\text{Standard deviation: } STD(X) = \frac{1}{N-1} \sum_{i \in N-1} (X(i) - \text{mean}(X))$$

$$\text{Signal Variation} = \frac{\text{mean}(X)}{STD(X)}$$

$$\text{Signal Variability} = \frac{\max(X - \text{mean}(X))}{\text{mean}(X)}$$

where, X is a sub-component or combined sub-component ratio derived from parameters as previously described, N is a calculation window size (there are N heart beat cycles in a shifting calculation window).

Figure 8:
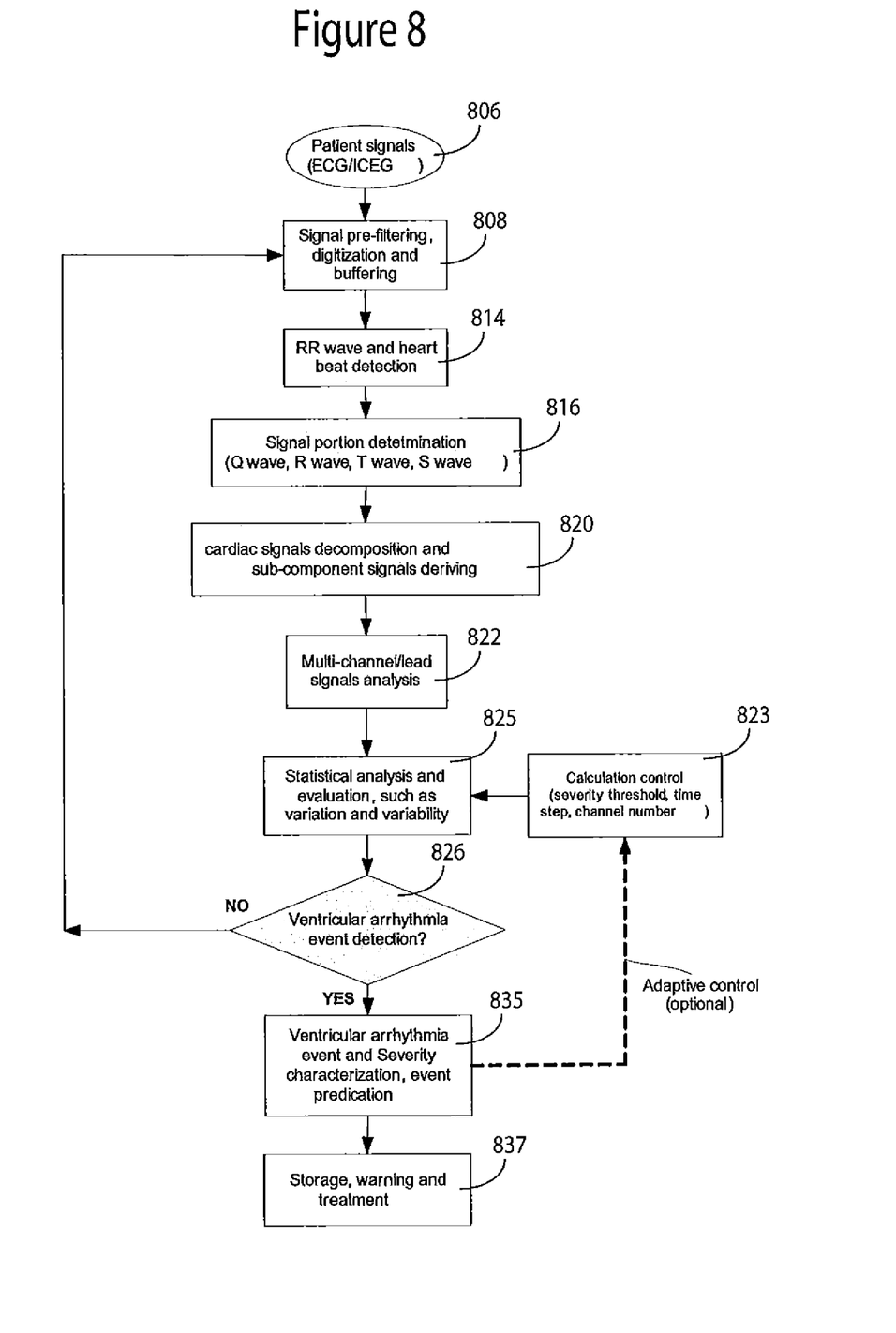
FIG. 8 shows a flowchart of a process performed by the system for calculating signal component parameters and monitoring and characterizing ventricular function status, according to invention principles.

FIG. 8 shows a flowchart of a process performed by system 10 for calculating signal component parameters and monitoring and characterizing ventricular function status. Interface 12 in step 808 provides sampled heart activity data by buffering and digitizing an electrical signal (such as an ECG or ICEG ventricular signal) received in step 806 and indicating electrical activity of a patient heart over multiple heart cycles. Interface 12 filters the sampled data using a filter for attenuating power line noise, respiration and patient movement noise. The filter is adaptively selected in response to data indicating clinical application (e.g. ischemia detection application, rhythm analysis application). In step 814, signal processor 15 identifies heart cycles (RR cycles) and different segments (QRS, P wave, Q wave, R wave, S wave, ST segment, T wave, U wave segments, for example) of the filtered sampled data signal. In step 820 filter 22 extracts depolarization and repolarization components. Specifically, in one embodiment filter 22 identifies first signal component data in a first selected bandwidth and first heart cycle portion (e.g., ventricular depolarization portion) of the received filtered sampled data and second signal component data in a different second selected bandwidth and second heart cycle portion (e.g., ventricular repolarization portion) of the received filtered sampled data.

Filter 22 uses a peak detector and time detector for identifying the peaks and wave segments. Filter 22 detects peaks of ECG and ICEG waveforms within received sampled data by synchronization of a heart electrical activity waveform and peak detection of a wave using a known peak detector and by identifying peaks of other waves by segmenting the signal represented by the sampled data into windows where the waves are expected and identifying the peaks within the windows. The start point of a wave, for example, is identified by a variety of known different methods. In one method a wave start point comprises where the signal crosses a baseline of the signal (in a predetermined wave window, for example).

Alternatively, a wave start point may comprise a peak or valley of signal. The baseline of the signal may comprise a zero voltage line if a static (DC) voltage signal component is filtered out from the signal. Filter 22 includes a timing detector for determining time duration between the signal peaks and valleys. The time detector uses a clock counter for counting a clock between the peak and valley points and the counting is initiated and terminated in response to the detected peak and valley characteristics.

In step 822 signal processor 15 uses the received filtered sampled data in calculating a ratio of a first value derived from said first signal component data to a second value derived from said second signal component data. Processor 15 calculates multiple ratios for sampled data from multiple different channels of a basket catheter or multiple cardiac catheters for example, to determine particular impaired cardiac tissue areas. Different signal data provided by different channels have different sensitivity. Processor 15 also determines and calculates other parameters and ratios for ventricular signal analysis including the parameters and ratios of FIGS. 4, 6 and 7 as well as an energy ratio to entropy ratio and ventricular signal ratio index $\Re_{Ventricle}$. Processor 15 in step 825 analyzes these parameters and ratios by performing a statistical analysis and calculating mean or average value, standard deviation, signal variation and signal variability using the functions previously described.

In step 826, signal processor 15 employs mapping information, associating ranges of the measured parameters and ratios of FIGS. 4, 6 and 7 with corresponding medical conditions (e.g., ischemia) in determining patient medical conditions, events and patient health status. If signal processor 15 and comparator 20 in step 826 determine a medical condition such as ventricular arrhythmia or related event indicating cardiac impairment or another abnormality is identified, processor 15 in step 835 uses the mapping information in determining severity, type and location of a cardiac condition. Patient monitor 19 in step 837 generates an alert message identifying the medical condition and abnormality and communicates the message to a user and stores data indicating the identified condition and associated calculated parameters in repository 17.

Processor 15 in step 823 selects a signal channel of a multi-channel catheter for use as signal input and adaptively adjusts the number of heart cycles in a calculation window used for averaging and adjusts the selected portions and ROI of a filtered signal analyzed and adjusts a threshold employed by comparator 20 to improve medical condition detection. In the analysis, processor 15 selects a severity threshold, calculation time step, monitored tissue location in response to user command or automatic system adaptive adjustment. The multi-channel patient signals include different lead signals or surface ECG signals or different channels (unipolar or bipolar) ICEG signals. If signal processor 15 and comparator 20 in step 826 do not identify a medical condition, the process is repeated from step 808. System 10 identifies and monitors different kinds of clinical events and cardiac pathology using the measured calculated parameters and ratios.

Figure 9:
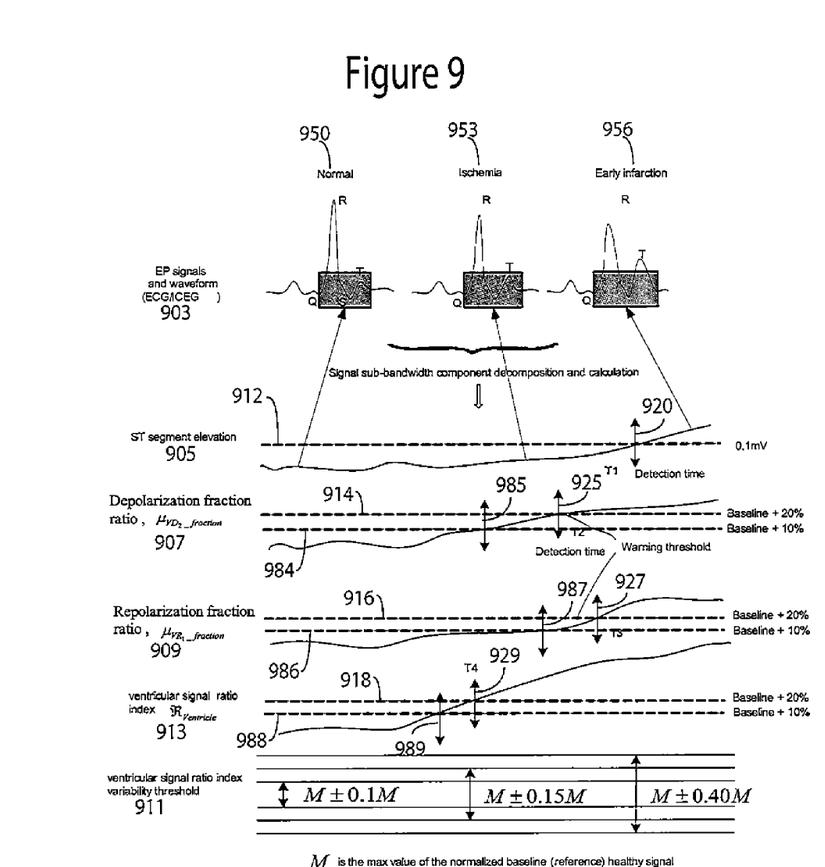
FIG. 9 shows ventricular arrhythmia (left ventricular ischemia and infarction) detection based on depolarization and repolarization signal and activity analysis and characterization, according to invention principles.

FIG. 9 shows ventricular arrhythmia (left ventricular ischemia and infarction) detection based on depolarization and repolarization signal and activity analysis and characterization. In the cardiac signal ratio calculation, the parameters in calculations may be adjusted in response to user or device command. Different bandwidth sub-component signals within ventricular electrophysiological signals provide different information. In different kinds of clinical application, different sub-component signals and ratios are utilized. For example, in early ventricular myocardial ischemia, a 20-40

Hz sub-component signal in ventricular depolarization shows substantial variation. While, in an early infarction stage (late ischemia event), relatively high frequency component signals of a ventricular depolarization portion and middle or high frequency component signals of a ventricular repolarization portion demonstrate obvious changes and deviation for ventricular arrhythmia pathology detection.

The system performs ventricular depolarization and repolarization signal and sub-bandwidth component ratio quantification and characterization to detect different kinds of clinical events and cardiac pathologies in a ventricle, such as myocardial ischemia, myocardial infraction, ventricular tachycardia and ventricular fibrillation. In the example, the system performs different calculations and statistical analysis, including determination of standard ST segment voltage deviation, depolarization fraction ratio $\mu_{VD_2\_fraction}$ ventricular repolarization fraction ratio $\mu_{VR_1\_fraction}$, and ventricular signal ratio index $\Re_{Ventricle}$ and corresponding variability, for comparison, such as time of pathology event detection, ischemia to infraction transition and severity characterization.

FIG. 9 shows a simulated ischemia event data analysis involving normal 950, ischemia 953 and early infarction 956 stages of an EP (electrophysiological) signal waveform 903. Processor 15 calculates and plots different types of parameter including, standard ST segment elevation 905, depolarization fraction ratio $\mu_{VD_2\_fraction}$ 907, ventricular repolarization fraction ratio $\mu_{VR_1\_fraction}$ 909 and ventricular signal ratio index $\Re_{Ventricle}$ 913 and corresponding variability. System 10 adaptively determines thresholds based on baseline normal parameter values and warning value levels to detect small changes within a ventricular waveform and associated trends. The severity of ongoing ventricular activity is determined using calculated ratios and predetermined warning thresholds. For example, a threshold value (e.g. 20%) has an assigned severity value of 10 for detection of the myocardial ischemia and normal severity value is 0 (normal). A 10% threshold change of the ratio has an assigned severity value of 5. The higher the severity value, the more severe and critical is the patient ventricular function abnormality. The ST segment elevation waveform 905 exceeds the detection threshold of 0.1 mV 912 at time T1 920 identifying myocardial ischemia (at this time, it may be in an early stage of myocardial infarction).

Processor 15 selects depolarization fraction ratio $\mu_{VD_2\_fraction}$ 907, ventricular repolarization fraction ratio $\mu_{VR_1\_fraction}$ 909 and ventricular signal ratio index $\Re_{Ventricle}$ 913 for use in detection. Processor 15 adaptively selects warning thresholds baseline +20% 914, 916 and 918 and baseline +10% 984, 986 and 988 separately in response to type of clinical application or procedure being performed. With these two thresholds, the myocardial ischemia is detected at T2 925, T3 927 and T4 929 (+20% threshold) and at times 985, 987 and 989 (+10% threshold) during the ischemia phase 953 and early infarction phase 956, and about 25 and 20 seconds earlier than the ST segment detection in phase 956. Processor 15 calculates ventricular signal index $\Re_{Ventricle}$ by combining different ratios with different weights (the weights are determined according to the significance of the ratio in a clinical application).

In one embodiment, an artificial neural network is used to train and derive an optimum weight coefficient set). In an example, 3 sub-bandwidth component signals are utilized, 20-40 Hz ventricular depolarization $VD_2$, 10-20 Hz ventricular repolarization $VR_2$, and 40-80 Hz ventricular depolarization $VD_3$ signals. In an $\Re_{Ventricle}$ calculation (the threshold is predetermined at baseline both +10% and +20%), the myocardial ischemia event can be detected at T4 929, which is about 50 seconds earlier than ST segment analysis. The ventricular sub-bandwidth component signals ratios provide advantageous ventricular function monitoring and the thresholds in the calculation are determined by a user or the system. Variability thresholds 911 of 0.1, 0.15 and 0.4 of the maximum value of the $\Re_{Ventricle}$ calculated value are adaptively selected and used in the three phases 950, 953 and 956. The severity of ongoing ventricular functions is indicated by calculated ratios and predetermined warning thresholds.

There are different kinds of ventricular parameter and ratio analysis for cardiac ischemia analysis and characterization. A system uses calculations independently. For example, sub-bandwidth component signal energy or energy fraction ratios may be used in an implantable cardiac device, which may require a low complexity system and relatively simple calculations. The systems uses ventricular sub-bandwidth component ratio based ischemia detection and analysis to identify cardiac disorders, differentiate cardiac arrhythmias, characterize pathological severity, predict of life-threatening events, and guides heart medical treatment, such as drug delivery and long term cardiac care and Holster Monitoring.

Figure 10:
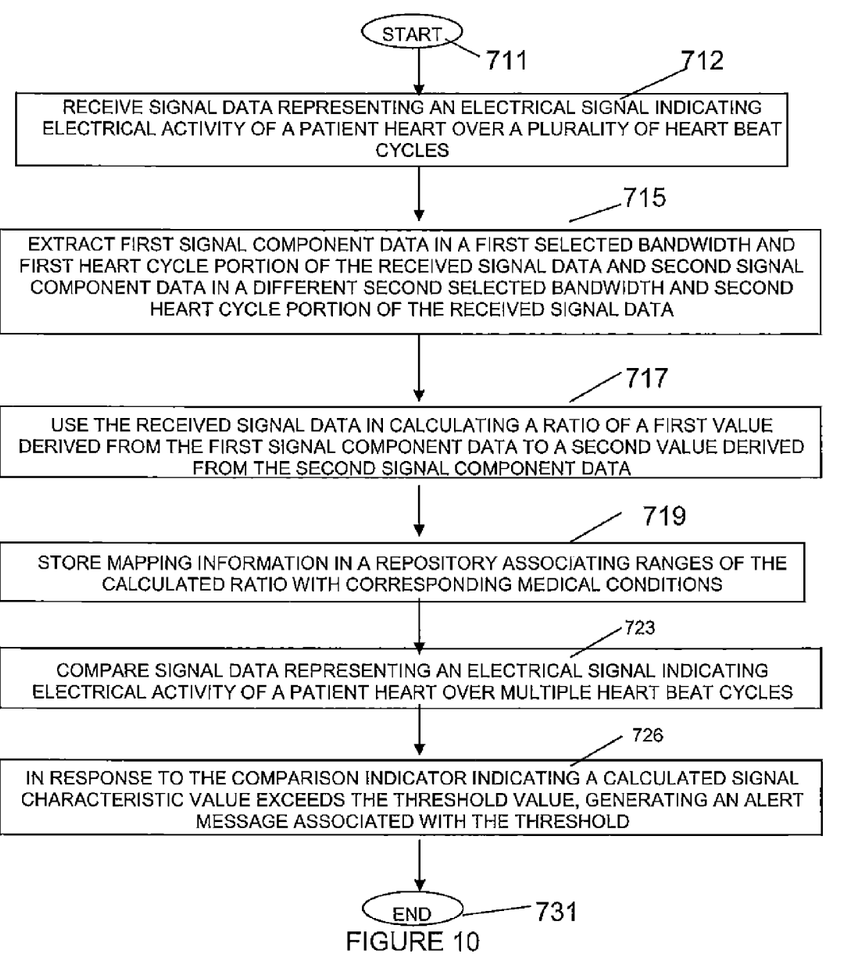
FIG. 10 shows a flowchart of a process used by a system for heart performance characterization and abnormality detection, according to invention principles.

FIG. 10 shows a flowchart of a process used by system 10 for heart performance characterization and abnormality detection. In step 712 following the start at step 711, interface 12 receives signal data (digitally sampled data) representing an electrical signal indicating electrical activity of a patient heart over multiple heart beat cycles. Filter 22 in step 715 extracts first signal component data in a first selected bandwidth and first heart cycle portion of the received signal data and second signal component data in a different second selected bandwidth and second heart cycle portion of the received signal data. In step 717 signal processor 15 uses the received signal data in calculating a ratio of a first value derived from the first signal component data to a second value derived from the second signal component data.

In one embodiment, the first value and second value are energy values and the first and second heart cycle portions comprise a depolarization procedure associated portion of a heart cycle. The energy values are calculated using a function of the form, $$\text{Energy: } E(\text{sub\_bandwidth\_component\_signal}) = \sum_{i \in \text{signal\_Q}} |V_Q(i)|^2$$

Where the sub_bandwidth_signal is a ventricular depolarization associated signal, $V_Q(i)$ is a discrete digitized value set of ventricular sub-component signal Q (depolarization). In one embodiment, the first and second selected bandwidths are substantially the same bandwidths and the first heart cycle portion comprises a depolarization procedure associated portion of a heart cycle and the second heart cycle portion comprises the QRS wave and T wave portion of a heart cycle. In a further embodiment, the first heart cycle portion comprises a depolarization procedure associated portion of a heart cycle and the second heart cycle portion comprises a repolarization procedure associated portion of a heart cycle. In a further embodiment, the first and second heart cycle portions comprise a repolarization procedure associated portion of a heart cycle. In an alternative arrangement, the first and second selected bandwidths are substantially the same bandwidths and the first heart cycle portion comprises a repolarization procedure associated portion of a heart cycle and the second heart cycle portion comprises the QRS wave and T wave portion of a heart cycle.

In another embodiment, the first value and second value are entropy values and the first and second heart cycle portions comprise a depolarization procedure associated portion of a heart cycle. The entropy values are calculated using a function of the form, $$\text{entropy}(\text{sub\_bandwidth\_signal}) = -\sum_{\substack{i=1 \\ x \in \text{sub\_bandwidth\_component}}}^{Z} p(x_i) \log(p(x_i))$$

where the sub_bandwidth_signal is a ventricular depolarization associated signal, $x_i$ is discrete digital data within the sub_bandwidth_signal, $p(x_i)$ is the probability of the x, within the sub_bandwidth_signal; Z is the total number of the digital data set of the sub_bandwidth_signal. The first and second selected bandwidths are substantially the same bandwidths and the first heart cycle portion comprises a depolarization procedure associated portion of a heart cycle and the second heart cycle portion comprises the QRS wave and T wave portion of a heart cycle. In a further embodiment, the first heart cycle portion comprises a depolarization procedure associated portion of a heart cycle and the second heart cycle portion comprises a repolarization procedure associated portion of a heart cycle. In a further embodiment, the first and second heart cycle portions comprise a repolarization procedure associated portion of a heart cycle. In another arrangement, the first and second selected bandwidths are substantially the same bandwidths and the first heart cycle portion comprises a repolarization procedure associated portion of a heart cycle and the second heart cycle portion comprises the QRS wave and T wave portion of a heart cycle.

Signal processor 15 calculates a standard deviation of the calculated ratio over multiple heart cycles and in step 719 stores mapping information in repository 17, associating ranges of the calculated ratio with corresponding medical conditions. The predetermined mapping information associates ranges of a calculated ratio with particular patient demographic characteristics and with corresponding medical conditions and the system uses patient demographic data including at least one of, age weight, gender and height in comparing the ratio with the ranges and generating an alert message indicating a potential medical condition.

In step 723, comparator 20 compares the calculated ratio or value derived from the calculated ratio with a threshold value to provide a comparison indicator identifying a medical condition. The threshold value is derived from recorded electrical signal data for the patient or is alternatively derived from recorded electrical signal data for a population of patients. The population of patients has similar demographic characteristics including at least two of, (a) age, (b) weight, (c) gender and (d) height, to those of the patient. Processor 15 in one embodiment dynamically adjusts the threshold value in response to a determined sensitivity of arrhythmia detection. In step 726 patient monitor 19 in response to the comparison indicator indicating a calculated signal characteristic value exceeds the threshold value, generates an alert message associated with the threshold identifying the medical condition. The process of FIG. 10 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system performs a sub-bandwidth signal measurement and ratio calculation including a Sub-bandwidth component signal energy ratio and Sub-bandwidth component signal entropy ratio. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both.

What is claimed is:

1. A system for heart performance characterization and abnormality detection for a patient, comprising:
   an interface configured to receive signal data representing an electrical signal indicating electrical activity of a patient heart over a plurality of heart beat cycles;
   a filter configured to extract:
      first signal component data in a first selected bandwidth and first heart cycle portion of the received signal data and
      second signal component data in a different second selected bandwidth and second heart cycle portion of the received signal data;
   a signal processor configured to:
      determine a first value based on the first signal component data, the first value comprising a first energy value derived from the first signal component data or a first entropy value derived from the first signal component data, and
      determine a second value based on the second signal component data, the second value comprising second energy value derived from the second signal component data or a second entropy value derived from the first signal component data;
      calculate a ratio of the first value to the second value;
   a comparator configured to compare the calculated ratio or a value derived from the calculated ratio with a threshold value to provide a comparison indicator; and
   a patient monitor configured to generate, in response to said comparison indicator indicating a calculated signal characteristic value exceeds the threshold value, an alert message associated with the threshold.

2. A system according to claim 1, wherein said signal data is digitally sampled data.

3. A system according to claim 1, wherein the first value and second value are energy values and the first and second heart cycle portions comprise a depolarization procedure associated portion of a heart cycle.

4. A system according to claim 3, wherein the energy values are calculated using a function of the form, $$\text{Energy: } E(\text{sub\_bandwidth\_component\_signal}) = \sum_{i \in signal\_Q} |V_Q(i)|^2$$

Where the sub_bandwidth_signal is a ventricular depolarization associated signal, $V_Q(i)$ is a discrete digitized value set of ventricular sub-component signal Q (depolarization).

5. A system according to claim 1, wherein the first value and second value are entropy values and the first and second heart cycle portions comprise a depolarization procedure associated portion of a heart cycle.

6. A system according to claim 5, wherein the entropy values are calculated using a function of the form, $$\text{entropy}(\text{sub\_bandwidth\_signal}) = -\sum_{\substack{i=1 \\ x \in sub\_bandwidth\_component}}^{z} p(x_i) \log(p(x_i))$$

where the sub_bandwidth_signal is a ventricular depolarization associated signal, $x_i$ is discrete digital data within the sub_bandwidth_signal, $p(x_i)$ is the probability of the $x_i$ within the sub_bandwidth_signal; Z is the total number of the digital data set of the sub_bandwidth_signal.

7. A system according to claim 1, wherein the first value and second value are energy values, the first and second selected bandwidths are substantially the same bandwidths and the first heart cycle portion comprises a depolarization procedure associated portion of a heart cycle and the second heart cycle portion comprises the QRS wave and T wave portion of a heart cycle.

8. A system according to claim 1, wherein the first value and second value are entropy values, the first and second selected bandwidths are substantially the same bandwidths and the first heart cycle portion comprises a depolarization procedure associated portion of a heart cycle and the second heart cycle portion comprises the QRS wave and T wave portion of a heart cycle.

9. A system according to claim 1, wherein the first value and second value are energy values, the first heart cycle portion comprises a depolarization procedure associated portion of a heart cycle and the second heart cycle portion comprises a repolarization procedure associated portion of a heart cycle.

10. A system according to claim 1, wherein the first value and second value are entropy values, the first heart cycle portion comprises a depolarization procedure associated portion of a heart cycle and, the second heart cycle portion comprises a repolarization procedure associated portion of a heart cycle.

11. A system according to claim 1, wherein the first value and second value are energy values and the first and second heart cycle portions comprise a repolarization procedure associated portion of a heart cycle.

12. A system according to claim 1, wherein the first value and second value are entropy values and the first and second heart cycle portions comprise a repolarization procedure associated portion of a heart cycle.

13. A system according to claim 1, wherein the first value and second value are energy values, the first and second selected bandwidths are substantially the same bandwidths and the first heart cycle portion comprises a repolarization procedure associated portion of a heart cycle and the second heart cycle portion comprises the QRS wave and T wave portion of a heart cycle.

14. A system according to claim 1, wherein the first value and second value are entropy values, the first and second selected bandwidths are substantially the same bandwidths and the first heart cycle portion comprises a repolarization procedure associated portion of a heart cycle and the second heart cycle portion comprises the QRS wave and T wave portion of a heart cycle.

15. A system according to claim 1, wherein said threshold value is derived from recorded electrical signal data for said patient.

16. A system according to claim 1, wherein said threshold value is derived from recorded electrical signal data for a population of patients.

17. A system according to claim 16, wherein said population of patients has similar demographic characteristics including at least two of, (a) age, (b) weight (c) gender and (d) height, to those of said patient.

18. A system according to claim 1, wherein said signal processor dynamically adjusts said threshold value in response to a determined sensitivity of arrhythmia detection.

19. A system according to claim 1, wherein
said signal processor calculates a standard deviation of the calculated ratio over a plurality of heart cycles and
said patient monitor, in response to an additional comparison indicator indicating a calculated standard deviation value exceeds a predetermined threshold value, generates an additional alert message.

20. A system according to claim 1, including
a repository of mapping information, associating ranges of the calculated ratio with corresponding medical conditions and
said comparator compares the calculated ratio with said ranges to provide a second comparison indicator identifying a medical condition and
said patient monitor generates a second alert message identifying said medical condition.

21. A system according to claim 20, wherein
said mapping information associates ranges of a calculated ratio with particular patient demographic characteristics and with the corresponding medical conditions and said system uses patient demographic data including at least one of, age weight, gender and height in comparing the ratio with said ranges and generating a third alert message indicating a potential medical condition.

22. A system for heart performance characterization and abnormality detection, comprising:
an interface configured to receive signal data representing an electrical signal indicating electrical activity of a patient heart over a plurality of heart beat cycles;
a filter configured to extract first signal component data in a first selected bandwidth and first heart cycle portion of the received signal data and second signal component data in a different second selected bandwidth and second heart cycle portion of the received signal data;
a signal processor configured to:
determine a first value based on the first signal component data, the first value comprising a first energy value derived from the first signal component data or a first entropy value derived from the first signal component data, and
determine a second value based on the second signal component data, the second value comprising second energy value derived from the second signal component data or a second entropy value derived from the first signal component data;
calculate a ratio of the first value to the second value; and
a patient monitor configured to generate, in response to comparing the calculated ratio or value derived from the calculated ratio with a threshold value, an alert message associated with the threshold.

23. A method for heart performance characterization and abnormality detection, the method comprising:
receiving signal data representing an electrical signal indicating electrical activity of a patient heart over a plurality of heart beat cycles;
extracting first signal component data in a first selected bandwidth and first heart cycle portion of the received signal data and second signal component data in a different second selected bandwidth and second heart cycle portion of the received signal data;
determining a first value based on the first signal component data, the first value comprising a first energy value derived from the first signal component data or a first entropy value derived from the first signal component data, and
determining a second value based on the second signal component data, the second value comprising second energy value derived from the second signal component data or a second entropy value derived from the first signal component data;
calculating a ratio of the first value to the second value;
in response to comparing the calculated ratio or a value derived from the calculated ratio with a threshold value, generating an alert message associated with the threshold.

* * * * *